US009364601B2

(12) United States Patent
Ichim et al.

(10) Patent No.: US 9,364,601 B2
(45) Date of Patent: *Jun. 14, 2016

(54) EXTRACORPOREAL REMOVAL OF MICROVESICULAR PARTICLES

(71) Applicant: Aethlon Medical, Inc., San Diego, CA (US)

(72) Inventors: Thomas Ichim, San Diego, CA (US); Richard H. Tullis, Encinitas, CA (US)

(73) Assignee: Aethlon Medical, Inc., San Diego, CA (US)

( * ) Notice: Subject to any disclaimer, the term of this patent is extended or adjusted under 35 U.S.C. 154(b) by 938 days.

This patent is subject to a terminal disclaimer.

(21) Appl. No.: 13/623,662

(22) Filed: Sep. 20, 2012

(65) Prior Publication Data

US 2013/0015118 A1    Jan. 17, 2013

Related U.S. Application Data

(62) Division of application No. 12/282,152, filed as application No. PCT/US2007/006101 on Mar. 9, 2007, now Pat. No. 8,288,172.

(60) Provisional application No. 60/780,945, filed on Mar. 9, 2006.

(51) Int. Cl.
| *G01N 33/543* | (2006.01) |
| *A61M 1/36* | (2006.01) |
| *B01D 15/00* | (2006.01) |
| *B01J 20/28* | (2006.01) |
| *B01J 20/32* | (2006.01) |
| *A61M 1/34* | (2006.01) |
| *A61M 1/16* | (2006.01) |

(52) U.S. Cl.
CPC ............... *A61M 1/362* (2014.02); *A61M 1/16* (2013.01); *A61M 1/3496* (2013.01); *A61M 1/3679* (2013.01); *B01D 15/00* (2013.01); *B01J 20/28014* (2013.01); *B01J 20/3242* (2013.01)

(58) Field of Classification Search
None
See application file for complete search history.

(56) References Cited

U.S. PATENT DOCUMENTS

| 3,925,152 | A | 12/1975 | Porath et al. | |
| 4,708,713 | A | 11/1987 | Lentz | |
| 4,714,556 | A | 12/1987 | Ambrus et al. | |
| 4,787,974 | A | 11/1988 | Ambrus et al. | |
| 5,041,079 | A | 8/1991 | Rakashima et al. | |
| 5,567,588 | A | 10/1996 | Gold et al. | |
| 5,667,684 | A | 9/1997 | Motomura et al. | |
| 5,782,792 | A | 7/1998 | Jones et al. | |
| 6,231,536 | B1 | 5/2001 | Lentz | |
| 6,528,057 | B1 | 3/2003 | Ambrus et al. | |
| 6,812,023 | B1 * | 11/2004 | Lamparski | C12N 5/0639 435/325 |
| 6,946,255 | B1 | 9/2005 | Kayagaki et al. | |
| 7,993,660 | B2 * | 8/2011 | Hadden | A61K 1/4439 424/278.1 |
| 8,021,847 | B2 * | 9/2011 | Pietrzkowski | C12Q 1/6806 435/6.12 |
| 8,288,172 | B2 * | 10/2012 | Ichim | A61M 1/3679 436/518 |
| 2004/0175291 | A1 | 9/2004 | Tullis et al. | |
| 2004/0197314 | A1 * | 10/2004 | Delcayre | A61K 47/48246 424/93.21 |
| 2004/0214783 | A1 * | 10/2004 | Terman | A61K 39/0011 514/33 |
| 2005/0042272 | A1 * | 2/2005 | Hou | A61K 39/29 424/450 |
| 2005/0265996 | A1 | 12/2005 | Lentz | |
| 2006/0116321 | A1 * | 6/2006 | Robbins | A61K 35/16 424/85.2 |
| 2006/0121005 | A1 * | 6/2006 | Berenson | C12N 5/0636 424/93.7 |
| 2007/0122415 | A1 * | 5/2007 | Gupta | C07K 14/00 424/160.1 |
| 2007/0172900 | A1 * | 7/2007 | Cahill | C12Q 1/6886 435/7.23 |
| 2009/0004197 | A1 * | 1/2009 | Markovitz | C07K 16/18 424/141.1 |
| 2009/0148460 | A1 * | 6/2009 | Delcayre | A61K 39/0012 424/152.1 |
| 2009/0297498 | A1 * | 12/2009 | Wang | C07K 14/705 424/94.64 |
| 2010/0151480 | A1 * | 6/2010 | Taylor | G07F 17/3258 435/6.16 |
| 2010/0184046 | A1 * | 7/2010 | Klass | C12Q 1/6886 435/7.1 |
| 2010/0196426 | A1 * | 8/2010 | Skog | C12Q 1/6883 424/400 |
| 2011/0053157 | A1 * | 3/2011 | Skog | C12Q 1/6883 435/6.18 |
| 2011/0195426 | A1 * | 8/2011 | Russo | C12N 15/1017 435/6.17 |
| 2012/0164628 | A1 * | 6/2012 | Duffin | G01N 33/54366 435/5 |
| 2013/0203061 | A1 * | 8/2013 | Kuslich | G01N 33/57484 435/6.12 |
| 2013/0323756 | A1 * | 12/2013 | Tullis | G01N 33/5695 435/7.23 |
| 2014/0161810 | A1 * | 6/2014 | Ichim | A61M 1/3679 424/140.1 |
| 2014/0166578 | A1 * | 6/2014 | Ichim | A61M 1/3679 210/638 |

FOREIGN PATENT DOCUMENTS

| CA | 2453198 | 7/2005 |
| WO | WO 2004/064608 | 8/2004 |
| WO | WO 2006/012886 | 11/2006 |
| WO | WO 2007/103572 | 9/2007 |

OTHER PUBLICATIONS

Abrahams et al., "Epithelial ovarian cancer cells secrete functional Fas ligand", Cancer Res vol. (2003) 63:5573-5581.

(Continued)

*Primary Examiner* — Ann Lam
(74) *Attorney, Agent, or Firm* — Knobbe, Martens, Olson & Bear, LLP

(57) ABSTRACT

The invention described herein teaches methods of removing microvesicular particles, which include but are not limited to exosomes, from the systemic circulation of a subject in need thereof with the goal of reversing antigen-specific and antigen-nonspecific immune suppression. Said microvesicular particles could be generated by host cells that have been reprogrammed by neoplastic tissue, or the neoplastic tissue itself. Compositions of matter, medical devices, and novel utilities of existing medical devices are disclosed.

17 Claims, No Drawings

(56) References Cited

OTHER PUBLICATIONS

Abusamra et al., "Tumor exosomes expressing Fas ligand mediate CD8+ T-cell apoptosis", Blood Cells Mol Dis (2005) 35:169-173.
Andreola et al., "Induction of lymphocyte apoptosis by tumor cell secretion of FasL-bearing microvesicles", J Exp Med (2002) 195:1303-1316.
Caby et al., "Exosomal-like vesicles are present in human blood plasma", Int Immunol (2005) 17:879-887.
Clayton et al., "Exosomes and the MICA-NKG2D system in cancer", Blood Cells Mol Dis (2005) 34:206-213.
Cuatrecasas et al., "Selective enzyme purification by affinity chromatography", Proc Natl Acad Sci USA (1968) 61(2):636-43.
Facciponte et al., "Heat shock proteins and scavenger receptors: role in adaptive immune responses", Immunol Invest (2005) 34:325-342.
Frangsmyr et al., "Cytoplasmic microvesicular form of Fas ligand in human early placenta: switching the tissue immune privilege hypothesis from cellular to vesicular level", Mol Hum Reprod (2005) 11:35-41.
Huang et al., "Survival, persistence, and progressive differentiation of adoptiveley transferred tumor-reactive T cells associated with tumor regression", J Immunother (2005) 28:258-267.
Ichim, "Revisiting immunosurveillance and immunostimulation: Implications for cancer immunotherapy", J Transl Med (2005) vol. 3 Issue 8.
Kacha et al., "Cutting edge: spontaneous rejection of poorly immunogenic P1. HTR tumors by Stat6-deficient mice", J Immunol (2000) 165:6024-6028.
Kim et al., "Fas ligand-positive membranous vesicles isolated from sera of patients with oral cancer induce apoptosis of activated T lymphocytes", Clin Cancer Res (2005) 11: 1 01 0-1 020.
Kobayashi, "Malignant neoplasms in registered cases of primary immunodeficiency syndrome", Jpn J Clin Oncol (1985) 15(1):307-312.
Lederer et al., "Cytokine transcriptional events during helper T cell subset differentiation", J Exp Med (1996) 184:397-406.
Llu et al., "Murine mammary carcinoma exosomes promote tumor growth by suppression of NK cell function", J Immunol (2006) 176: 1375-1385.
Loveland et al., "Mannan-MUC1-pulsed dendritic cell immunotherapy: a phase I trial in patients with adenocarcinoma", Clin Cancer Res (2006) 12:869-877.
Mincheva-Nilsson et al., "Placenta-Derived Soluble MHC Class I Chain-Related Molecules Down-Regulate NKG2D Receptor on Peripheral Blood Mononuclear Cells during Human Pregnancy: A Possible Novel Immune Escape Mechanism for Fetal Survival", J Immunol (2006) 176:3585-3592.
Morelli, "The immune regulatory effect of apoptotic cells and exosomes on dendritic cells: its impact on transplantation", Am J Transplant (2006) 6:254-261.
Mu et al., "Immunotherapy with allotumour mRNA-transfected dendritic cells in androgen-resistant prostate cancer patients", Br J Cancer (2005) 93:749-756.
Nakamura et al., "Genetic polymorph isms of the interleukin-4 receptor alpha gene are associated with an increasing risk and a poor prognosis of sporadic renal cell carcinoma in a Japanese population", Clin Cancer Res (2002) 8:2620-2625.
Oldford et al., "Tumor cell expression of HLA-DM associates with a Th1 profile and predicts imporved survival in breast carcinoma patients", Int Immunol (2006) 18:1591-1602.
Ostman et al., "Tolerosome-induced oral tolerance is MHC dependent", Immunology (2005) 116:464-476.
Ostrand-Rosenberg et al., "Cutting edge: STAT6-deficient mice have enhanced tumor immunity to primary and metastatic mammary carcinoma", J Immunol (2000) 165:6015-6019.
Ostrand-Rosenberg et al., "Resistance to metastatic disease in State-deficient mice requires hemopoietic and nonhemopoietic cells and is IFN-gamma dependent", J. Immunol (2002) 169:5796-5804.
Parmiani et al., "Unique human tumor antigens: immunobiology and use in clinical trials", J Immunol (2007) 178: 1975-1979.
Peche et al., "Presentation of donor major histocompatibility complex antigens by bone marrow dendritic cell-derived exosomes modulates allograft rejection", Transplantation (2003) 76: 1503-151.
Penn, "Depressed immunity and the development of cancer", Cancer Detect Prey (1994) 18:241-252.
Penn, "Occurrence of cancers in immunosuppressed organ transplant recipients", Clin Transpl (1994) 99-109.
Riteau et al., "Exosomes bearing HLA-G are released by melanoma cells", Hum Immunol (2003) 64: 1 064-1 072.
Sjogren et al., "Suggestive evidence that the 'blocking antibodies' of tumor-bearing individuals may be antigen--antibody complexes", Pro Natl Acad Sci USA (1971) 68: 1372-1375.
Taylor et al., "Pregnancy-associated exosomes and their modulation of T-cell signaling", (2006) J. Immunol176:1534-1542.
Taylor et al., "T-cell apoptosis and suppression of T-cell receptor/CD3-zeta by Fas ligand-containing membrane vesicles shed from ovarian tumors", Clin Cancer Res (2003) 9:5113-5119.
Taylor et al., "Tumour-derived exosomes and their role in cancer-associated T-cell signalling defects", Br J Cancer (2005) 92:305-311.
Valenti et al., "Human tumor-released microvesicles promote the differentiation of myeloid cells with transforming growth factor-beta-mediated suppressive activity on T lymphocytes", Cancer Res (2006) 66: 9290-9298.
Van Niel et al., "Intestinal epithelial exosomes carry MHC class II/peptides able to inform the immune system in mice", Gut (2003) 52:1690-1697.
Wang et al., "Recent advances in heat shock protein-based cancer vaccines", Hepatobiliary Pancreat Dis Int (2006) 5:22-27.
Whiteside, "Tumour-derived exosomes or mivrovesicles: another mechanism of tumour escape from the host immune system?", Br J Cancer (2005) 92:209-211.
Zhu et al., "GATA-3 promotes Th2 responses through three different mechanisms: induction of Th2 cytokine production, selective growth of Th2 cells and inhibition of Th1 cell-specific factors", Cell Res (2006) 16:3-10.
International Preliminary Report on Patentability for Application No. PCT/US07/0061 01, filed Mar. 9, 2007, mailed Sep. 18, 2008.
International Search Report and Written Opinion for PCT Application No. PCT/US07/061 01, filed Mar. 9, 2007, mailed Jun. 24, 2008.

\* cited by examiner

EXTRACORPOREAL REMOVAL OF MICROVESICULAR PARTICLES

RELATED APPLICATIONS

This application is a divisional application of U.S. Ser. No. 12/282,152 filed May 26, 2009 entitled "EXTRACORPOREAL REMOVAL OF MICROVESICULAR PARTICLES" which is the U.S. National Phase under 35 U.S.C. §371 of International Application No. PCT/US2007/006101 filed Mar. 9, 2007 which claims the benefit of U.S. Provisional Application No. 60/780,945 filed Mar. 9, 2006, the contents of which are incorporated herein by reference in their entireties.

FIELD OF THE INVENTION

The present invention relates to the field of therapeutic methods and devices for the extracorporeal removal of microvesicular particles, useful, for example, for reversing immune suppression in a subject in need thereof (e.g., a cancer patient) through extracorporeal means.

BACKGROUND OF THE INVENTION

Immunological control of neoplasia has been a topic of intense investigation dating back to the days of William Coley, who at the beginning of the 20$^{th}$ century reported potent induction of tumor remission through administration of various non-specific immune stimulatory bacterial extracts which came to be known as "Coley's Toxins" (1). Suggestions of the ability to induce anti-cancer immunological responses also came from experiments in the 1920s demonstrating that the vaccination with non-viable tumor cells mounts a specific "resistance" to secondary challenge, although at the time, the concept of MHC matching was not known and it was possible that the secondary resistance was only a product of allogeneic sensitization (2). Although the field of cancer immunotherapy has been very controversial throughout the 20$^{th}$ Century, with some authors actually claiming that immunological responses are necessary for tumor growth (3), the age of molecular biology has demonstrated that indeed immune responses are capable of controlling tumors from initiating, as well as in some cases inhibiting the growth of established tumors.

Originally demonstrated in the murine system, the concept of a productive anti-tumor response was associated with a cytokine profile termed Th1, whereas an ineffective anti-tumor response was associated with Th2. The prototypic method of assessing Th1 activity was by quantitation of the cytokine IFN-γ (4). At an epigenetic level it is known that the chromatin structure of Th1 and Th2 cells is distinct, thus providing a solid foundation that once a naïve T cell has differentiated into a Th1 or Th2 cell, the silenced and activated parts of the chromatin are passed to progeny cells, thus the phenotype is stable (5). Associated with such chromatin changes is the activation of the multi-gene inducing transcription factors GATA-3 (6), STAT6 (7, 8) in Th2 cells, and T-bet (9), and STAT4 (10) in Th1 cells. Accordingly studies have been performed using STAT6 knockout mice as a model of an immune response lacking Th2 influences, thus predominated by Th1. Tumors administered to STAT6 knockout animals are either spontaneously rejected (11), or immunity to them is achieved with much higher potency compared to wild-type animals (12). Furthermore immunologically mediated increased resistance to metastasis is observed (13). In agreement with the Th1/Th2 balance, mice lacking STAT4 develop accelerated tumors in a chemically-induced carcinogenesis model (14).

In the clinical situation correlation between suppressed immune responses and a higher incidence of cancer is well established. For example, natural immune deficiency such as the congenital abnormality Chediak-Higashi Syndrome, in which patients have abnormal natural killer cell function, is associated with an overall weakened immune response. In this population, the overall incidence of malignant tumors is 200-300 times greater than that in the general population (15). In another example, a specific polymorphism of the IL-4 receptor gene that is known to be associated with augmented Th2 responses was investigated in an epidemiological study. Multivariate regression analysis showed that the specific genotype of the IL-4R associated with augmented Th2 activity was an independent prognostic factor for shorter cancer survival and more advanced histopathological grade (16). In addition to inborn genetic abnormalities, the immune suppressive regimens used for post-transplant antirejection effect are associated with a selective inhibition of Th1 responses (17-19). In support of the concept that suppression of Th1 immunity is associated with cancer onset, the incidence of cancer in the post-transplant population is markedly increased in comparison to controls living under similar environmental conditions (20-25). In terms of disease associated immune suppression, HIV infected patients also have a marked predisposition to a variety of tumors, especially, but not limited to lymphomas, as a result of immunodeficiency (26).

Although the above examples support a relation between immune suppression (or Th2 deviation) and cancer, the opposite situation, of immune stimulation resulting in anticancer response, is also documented. Numerous clinical trials using antigen specific approaches such as vaccination with either tumor antigens alone (27, 28), tumor antigens bound to immunogens (29, 30), tumor antigens delivered alone (31) or in combination with costimulatory molecules by viral methods (32), tumor antigens loaded on dendritic cells ex vivo (33-35), or administration of in vitro generated tumor-reactive T cells (36), have all demonstrated some clinical effects. Unfortunately, to date, there is no safe, reproducible, and mass-applicable method of therapeutically inducing regression of established tumors, or metastasis via immunotherapy. Approved immunotherapeutic agents such as systemic cytokine administration are associated with serious adverse effects, as well as mediocre responses and applicability to a very limited patient subset.

Accordingly, there is a need in the art to develop successful immunotherapy capable of stimulating specific immune responses that only target neoplastic tissue, or components of the host tissue whose activity is necessary for the progression of neoplasia (ie endothelium). The development of such a successful immunotherapy is hindered by suppression of the host immune system by the cancer. Experiments in the 1970s demonstrated the existence of immunological "blocking factors" that antigen-specifically inhibited lymphocyte responses. Some of this early work involved culturing autologous lymphocytes with autologous tumor cells in the presence of third party healthy serum. This culture resulted in an inhibition of growth of the autologous tumor as a result of the lymphocytes. Third party lymphocytes did not inhibit the growth of the tumor. Interestingly when autologous serum was added to the cultures the lymphocyte mediated inhibition of tumor growth was not observed. These experiments gave rise to the concept of antigen-specific "blocking factors" found in the body of cancer patients that incapacitate successful tumor immunity (37-39).

More recent demonstration of tumor-suppression of immune function was seen in experiments showing that T cell function is suppressed in terms of inability to secrete interferon gamma due to a cleavage of the critical T cell receptor transduction component, the TCR-zeta chain. Originally, zeta chain cleavage was identified in T cells prone to undergo apoptosis. Although a wide variety of explanations have been put forth for the cleavage of the zeta chain, one particular cause was postulated to be tumor-secreted microvesicles.

Microvesicles secreted by tumor cells have been known since the early 1980s. They were estimated to be between 50-200 nanometers in diameter and associated with a variety of immune inhibitory effects. Specifically, it was demonstrated that such microvesicles could not only induce T cell apoptosis, but also block various aspects of T cell signaling, proliferation, cytokine production, and cytotoxicity. Although much interest arose in said microvesicles, little therapeutic applications developed since they were uncharacterized at a molecular level.

Research occurring independently identified another type of microvesicular-like structures, which were termed "exosomes". Originally defined as small (i.e., 80-200 nanometers in diameter), exosomes were observed initially in maturing reticulocytes. Subsequently it was discovered that exosomes are a potent method of dendritic cell communication with other antigen presenting cells. Exosomes secreted by dendritic cells were observed to contain extremely high levels of MHC I, MHC II, costimulatory molecules, and various adhesion molecules. In addition, dendritic cell exosomes contain antigens that said dendritic cell had previously engulfed. The ability of exosomes to act as "mini-antigen presenting cells" has stimulated cancer researchers to pulse dendritic cells with tumor antigens, collect exosomes secreted by the tumor antigen-pulsed dendritic cell, and use these exosomes for immunotherapy. Such exosomes were seen to be capable of eradicating established tumors when administered in various murine models. The ability of dendritic exosomes to potently prime the immune system brought about the question if exosomes may also possess a tolerance inducing or immune suppressive role. Since it is established that the exosome has a high concentration of tumor antigens, the question arose if whether exosomes may induce an abortive T cell activation process leading to anergy. Specifically, it is known that numerous tumor cells express the T cell apoptosis inducing molecule Fas ligand.

Fas ligand is an integral type II membrane protein belonging to the TNF family whose expression is observed in a variety of tissues and cells such as activated lymphocytes and the anterior chamber in the eye. Fas ligand induces apoptotic cell death in various types of cells target cells via its corresponding receptor, CD95/APO1. Fas ligand not only plays important roles in the homeostasis of activated lymphocytes, but it has also been implicated in establishing immune-privileged status in the testis and eye, as well as a mechanisms by which tumors escape immune mediated killing. Accordingly, given the expression of Fas ligand on a variety of tumors, we and others have sought, and successful demonstrated that Fas ligand is expressed on exosomes secreted by tumor cells (40).

Due to the ability of exosomes to mediate a variety of immunological signals, the model system was proposed that at the beginning of the neoplastic process, tumor secreted exosomes selectively induce antigen-specific T cell apoptosis, through activating the T cell receptor, which in turn upregulates expression of Fas on the T cell, subsequently, the Fas ligand molecule on the exosome induces apoptosis. This process may be occurring by a direct interaction between the tumor exosome and the T cell, or it may be occurring indirectly by tumor exosomes binding dendritic cells, then subsequently when T cells bind dendritic cells in lymphatic areas, the exosome actually is bound by the dendritic cell and uses dendritic cell adhesion/costimulatory molecules to form a stable interaction with the T cell and induce apoptosis. In the context of more advanced cancer patients, where exosomes reach higher concentrations systemically, the induction of T cell apoptosis occurs in an antigen-nonspecific, but Fas ligand, MHC I-dependent manner.

The recent recognition that tumor secreted exosomes are identical to the tumor secreted microvesicles described in the 1980s (41), has stimulated a wide variety of research into the immune suppressive ability of said microvesicles. Specifically, immune suppressive microvesicles were identified not only in cancer patients (42, 43), but also in pregnancy (44-46), transplant tolerance (47, 48), and oral tolerance (49, 50) situations.

Previous methods of inducing anti-cancer immunity have focused on stimulation of either innate or specific immune responses, however relatively little work has been performed clinically in terms of de-repressing the immune functions of cancer patients. Specifically, a cancer patient having tolerance-inducing exosomes has little chance of mounting a successful anti-tumor immune response. This may be one of the causes for mediocre, if not outright poor, results of current day immunotherapy.

Others have attempted to de-repress the immune system of cancer patients using extracorporeal removal of "blocking factors". Specifically, Lentz in U.S. Pat. No. 4,708,713 describes an extracorporeal method of removing proteins approximately 200 kDa, which are associated with immune suppression. Although Lentz has generated very promising results using this approach, the approach is: a) not-selective for specific inhibitors; b) theoretically would result in loss of immune stimulatory cytokines; c) is not applicable on a wide scale; and d) would have no effect against tumor-secreted microvesicles which are much larger than 200 kDa.

The recently discovered properties of microvesicles in general, and tumor microvesicles specifically, have made them a very promising target for extracorporeal removal. Properties such as upregulated expression of MHC I, Fas ligand, increased affinity towards lectins, and modified sphingomyelin content allow for use of extracorporeal devices to achieve their selective removal. Additionally, the size of microvesicles would allow for non-selective removal either alone or as one of a series of steps in selective removal.

SUMMARY OF THE INVENTION

In accordance with the present invention, there are provided methods of immune stimulation and/or immune de-repression using extracorporeal techniques to remove microvesicles from circulation.

In one aspect, the present invention relates to methods of removing microvesicles from the circulation of a subject in need thereof (e.g., cancer patients), thereby de-repressing immune suppression present in said subjects. Accordingly, the present invention teaches the use of various extracorporeal devices and methods of producing extracorporeal devices for use in clearing microvesicle content in subjects in need thereof. Said microvesicles may be elaborated by the tumor itself, or may be generated by non-malignant cells under the influence of tumor soluble or contact dependent interactions. Said microvesicles may be directly suppressing the host immune system through induction of T cell apoptosis, proliferation inhibition, incapacitation, anergy, deviation in cytokine production capability or cleavage of the T cell receptor zeta chain, or alternatively said microvesicles may be indirectly suppressing the immune system through modification of function of other immunological cells such as dendritic cells, NK cells, NKT cells and B cells. Said microvesicles may be suppressing the host antitumor immune response either in an antigen-specific or an antigen-nonspecific manner, or both.

One of the objects of the present invention is to provide an effective and relatively benign treatment for cancer.

Another object is to provide an adjuvant, and/or neoadjuvant therapy to be used in conjunction with currently used cancer treatments that require a functional immune response for efficacy.

Another object is to provide an adjuvant, and/or neoadjuvant therapy to be used in conjunction with currently used cancer treatments that stimulate the immune response of a subject in need thereof in an antigen-specific manner.

Another object is to provide an adjuvant, and/or neoadjuvant therapy to be used in conjunction with currently used cancer treatments that stimulate the immune response of a subject in need thereof in an antigen-nonspecific manner.

Another object is to provide improvements in extracorporeal treatment of cancer through selecting the novel target of tumor associated microvesicles.

Another object is to provide beads or other types of particles that can form a matrix outside of a hollow fiber filter, said matrix component having a size greater than pores of said hollow fiber filter, and said beads or other types of particles being bound to agents that capture microvesicles.

Another object is to provide improvements in extracorporeal treatment of cancer through selecting the novel target of tumor associated microvesicles containing unique properties that are not found on microvesicles found in non-cancer patients.

Another object is to provide improved specific affinity devices, particularly immunoadsorption devices, and methods useful for removal of cancer associated microvesicles from cancer patients. Specifically, immunoadsorption devices use proteins with affinity to components of the tumor associated microvesicles. Said proteins include antibodies such as antibodies to Fas ligand, MHC I, MHC II, CD44, placental alkaline phosphatase, TSG-101, MHC I-peptide complexes, MHC II-peptide complexes, or proteins found to be present on the exterior of microvesicles contributing to immune suppression found in a cancer patient. Contemplated within the invention are proteins that act as ligands for the microvesicular proteins, said proteins may be currently in existence, or may be generated by in silico means based on known qualities of microvesicle-specific proteins.

In accordance with one particular aspect of the present invention, methods and devices for treating cancer are provided that are based on the utilization of specific affinity adsorption of microvesicles that are associated with the cancerous state. The affinity adsorbents utilized in accordance with the present invention are both immunoadsorbents and non-immune-based specific affinity chemical adsorbents. More specifically, adsorption can be accomplished based on specific properties of the cancer associated microvesicles, one said property is preferential affinity to lectins and other sugar-binding compounds.

In one particular embodiment, the invention provides a device for extracorporeal treatment of blood or a blood fraction such as plasma. This device has a sorbent circulation circuit, which adheres to and retains microvesicles, and a blood circulation circuit through which blood cells flow unimpeded. The device may be constructed in several variations that would be clear to one skilled in the art. Specifically, the device may be constructed as a closed system in a manner that no accumulating reservoir is needed and the sorbent circulation system accumulates the microvesicles, while non-microvesicle matter is allowed to flow back into the blood circulation system and subsequently returned to the patient. Alternatively, the device may use an accumulator reservoir that is attached to the sorbent circulation circuit and connected in such a manner so that waste fluid is discarded, but volume replenishing fluid is inserted back into the blood circulation system so the substantially microvesicle purified blood that is reintroduced to said patient resembles a hematocrit of significant homology to the blood that was extracted from said patient.

DETAILED DESCRIPTION OF THE INVENTION

For the purposes of advancing and clarifying the principles of the invention disclosed herein, reference will be made to certain embodiments and specific language will be used to describe said embodiments. It will nevertheless be understood and made clear that no limitation of the scope of the invention is thereby intended. The alterations, further modifications and applications of the principles of the invention as described herein serve only as specific embodiment, however one skilled in the art to which the invention relates will understand that the following are indeed only specific embodiments for illustrative purposes, and will derive similar types of applications upon reading and understanding this disclosure.

In accordance with one aspect of the present invention, there are provided methods of removing microvesicular particles from a subject in need thereof, said methods comprising:

a) establishing an extracorporeal circulation system which comprises contacting the whole blood or components thereof with a single or plurality of agents capable of binding microvesicles found within said blood or components thereof; and b) returning said blood or components thereof into the original blood, said blood or blood components containing substantially less immune suppressive particles in comparison to the blood or blood components originally residing in the blood.

Invention methods are useful, for example, for de-repressing immune response, which includes restoration of one or more of the following: T cell, natural killer (NK) cell, natural killer T (NKT) cell, gamma-delta T cell, and B cell function. Presently preferred applications of invention methods include restoration of one or more of the following: T cell, natural killer (NK) cell, natural killer T (NKT) cell, gamma-delta T cell, and B cell function includes prevention of apoptosis; it is especially preferred that restoration of one or more of the following: T cell, natural killer (NK) cell, natural killer T (NKT) cell, gamma-delta T cell, and B cell function includes restoration and/or endowment of activity capable of inhibiting cancer progression.

Inhibiting cancer progression as contemplated herein is accomplished in a variety of ways, e.g., by one or more of the following: direct cytolysis of tumor cells, direct induction of tumor cell apoptosis, induction of tumor cell cytolysis through stimulation of intrinsic host antitumor responses, induction of tumor cell apoptosis through stimulation of intrinsic host antitumor responses, inhibition of tumor cell metastasis, inhibition of tumor cell proliferation, and induction of senescence in the tumor cell.

Exemplary tumor cells contemplated for treatment herein are selected from the group of cancers consisting of: soft tissue sarcomas, kidney, liver, intestinal, rectal, leukemias, lymphomas, and cancers of the brain, esophagus, uterine cervix, bone, lung, endometrium, bladder, breast, larynx, colon/rectum, stomach, ovary, pancreas, adrenal gland and prostate.

Agents capable of binding microvesicles contemplated for use herein are selected from the group consisting of one or more of the following: a) a singular or plurality of antibody species; b) a singular or plurality of proteins (e.g., lectins); c) a singular or plurality of aptamers, d) a surface that selectively restricts microvesicles from passage, and e) a surface with selective adhesion to microvesicles.

Antibodies contemplated for use herein have a specificity for proteins selected from the group consisting of one or more of the following: Fas ligand, MHC I, MHC II, CD44, placental alkaline phosphatase, TSG-101, MHC I-peptide complexes, MHC II-peptide complexes, and proteins found to be present on the exterior of microvesicles contributing to immune suppression found in a cancer patient. Presently preferred antibodies are specific to Fas ligand, MHC I, and the like.

Binding proteins contemplated for use herein are selected from the group comprising consisting of one or more of the following: Fas, T cell Receptor, protein extracts isolated from T cells, protein extracts isolated from dendritic cells, and proteins found to possess affinity for binding proteins found on microvesicles associated with immune suppression.

Surfaces contemplated for use herein that selectively restrict passage of said microvesicles typically have pore sizes in the range of about 20-400 nanometers in size, with surfaces having pore sized in the range of about 40-300 nanometers in size being preferred, with surfaces having a pore size in the range of about 50-280 nanometers in size being especially preserved.

Surfaces with selective adhesion to microvesicles contemplated for use herein can be coated with a single compound, or a plurality of compounds that bind particles that are enriched in sphingomyelin and with a lower level of phosphatidylcholine as found in the cellular membranes of non-malignant cells.

In accordance with another aspect of the present invention, agents capable of binding microvesicles are immobilized on a porous hollow fiber membrane. For example, agents capable of binding microvesicles are immobilized on the porous exterior of the hollow fiber membrane.

In accordance with another aspect of the present invention, existing methods and devices of extracorporeal treatment of blood can be integrated (in whole or in part) with the above-described methods to augment ex vivo clearance of microvesicles in a physiologically applicable manner. For example, existing methods for extracorporeal treatment of blood can be selected from one or more of the following: a) hemofiltration; b) hemodialysis; and c) hemodiafiltration. A presently preferred existing method for extracorporeal treatment of blood comprises apheresis followed by filtration.

In accordance with another embodiment of the present invention, there are provided medical devices useful for the removal of cancer associated microvesicles from the blood of a cancer patient, said device comprising:

a) an intake conduit through which blood of a cancer patient in need of treatment enters;

b) a single or plurality of matrices capable of adhering to microvesicles causative of cancer associated immune suppression; and c) a system for reintroduction of said blood into the patient in need thereof, whereby said blood is reintroduced under physiologically acceptable conditions.

In one aspect of the above-described medical device, the matrices surround a plurality of hollow fiber filters. Preferably, the hollow fiber filters have a diameter of sufficient size to allow passage of blood cells through the lumen, and diffusion of particles between 80-300 nanometers in size.

In another aspect of the above-described medical device, a microvesicle binding agent is chemically reacted with a high-molecular weight substrate and placed on the exterior of said hollow fibers so as to bind non-blood cell liquids permeating through the pores of said hollow fibers. Exemplary microvesicle binding agents include one or more of the following: a) a singular or plurality of antibody species; b) a singular or plurality of proteins (e.g., lectins); c) a singular or plurality of aptamers, d) a surface that selectively restricts microvesicles from passage, and e) a surface with selective adhesion to microvesicles.

Exemplary antibodies contemplated for use herein have a specificity for proteins selected from the group consisting of one or more of the following: Fas ligand, MHC I, MHC II, CD44, placental alkaline phosphatase, TSG-101, MHC I-peptide complexes, MHC II-peptide complexes, and proteins found to be present on the exterior of microvesicles contributing to immune suppression found in a cancer patient. Presently preferred antibodies are specific to Fas ligand, MHC I, and the like.

Exemplary proteins contemplated for use in the invention device are selected from the group consisting of one or more of the following: Fas, T cell Receptor, protein extracts isolated from T cells, protein extracts isolated from dendritic cells, and proteins found to possess affinity for binding proteins found on microvesicles associated with immune suppression.

In accordance with another embodiment of the present invention, there are provided methods of potentiating the immunologically mediated anticancer response elicited by vaccination to tumor antigens, said methods comprising:

a) immunizing a subject in need thereof using a single or combination of tumor antigens;

b) removing immunosuppressive microvesicles from the sera of said subject by extracorporeal means; and c) adjusting the amount of removal of immune suppressive microvesicles based on immune stimulation desired.

In accordance with yet another embodiment of the present invention there are provided methods of enhancing the immune response of a subject in need thereof through the removal of microvesicular particles found in systemic circulation of said subject, said methods comprising:

a) establishing an extracorporeal circulation system which comprises contacting the whole blood or components thereof with a single or plurality of agents capable of binding microvesicles found within said blood or components thereof; and b) returning said blood or components thereof into the subject, said blood or blood components containing substantially less immune suppressive particles in comparison to the blood or blood components originally residing in said subject.

Enhancing immune response as contemplated herein includes one or more of the following: upregulation of T cell, natural killer (NK) cell, natural killer T (NKT) cell, gamma-delta T cell, and B cell function. In a presently preferred embodiment, upregulation of one or more of T cell, natural killer (NK) cell, natural killer T (NKT) cell, gamma-delta T cell, and B cell function includes prevention of apoptosis. In yet another preferred embodiment, upregulation of one or more of T cell, natural killer (NK) cell, natural killer T (NKT) cell, gamma-delta T cell, and B cell function includes enhancing and/or endowment of activity capable of inhibiting cancer progression.

Inhibiting cancer progression contemplated herein is accomplished in a variety of ways, e.g., by direct cytolysis of tumor cells, direct induction of tumor cell apoptosis, induction of tumor cell cytolysis through stimulation of intrinsic host antitumor responses, induction of tumor cell apoptosis through stimulation of intrinsic host antitumor responses, inhibition of tumor cell metastasis, inhibition of tumor cell proliferation, and induction of senescence in the tumor cell.

Tumor cells contemplated for treatment in accordance with the present invention are selected from the group of cancers consisting of soft tissue sarcomas, kidney, liver, intestinal, rectal, leukemias, lymphomas, and cancers of the brain, esophagus, uterine cervix, bone, lung, endometrium, bladder, breast, larynx, colon/rectum, stomach, ovary, pancreas, adrenal gland and prostate.

Agents capable of binding microvesicles contemplated for use herein are selected from the group consisting of one or more of the following: a) a singular or plurality of antibody species; b) a singular or plurality of proteins (e.g., lectins); c) a singular or plurality of aptamers, d) a surface that selectively restricts microvesicles from passage, and e) a surface with selective adhesion to microvesicles.

Antibodies having specificity for proteins contemplated for use herein are selected from the group consisting of one or more of the following: Fas ligand, MHC I, MHC II, CD44, placental alkaline phosphatase, TSG-101, MHC I-peptide complexes, MHC II-peptide complexes, and proteins found to be present on the exterior of microvesicles contributing to immune suppression found in a cancer patient. Presently preferred antibodies are specific to Fas ligand, MHC I, and the like.

Proteins contemplated for use herein are selected from the group consisting of one or more of the following: Fas, T cell Receptor, protein extracts isolated from T cells, protein extracts isolated from dendritic cells, and proteins found to possess affinity for binding proteins found on microvesicles associated with immune suppression.

Surfaces that selectively restrict passage of said microvesicles contemplated for use herein typically have a pore size in the range of about 20-400 nanometers in size, with pores sizes in the range of about 40-300 nanometers in size being preferred, and pore sizes in the range of about 50-280 nanometers in size being especially preferred.

Surfaces with selective adhesion to microvesicles contemplated for use herein are coated with a variety of agents, e.g., a single compound, or plurality of compounds that bind particles that are enriched in sphingomyelin and with a lower level of phosphatidylcholine as found in the cellular membranes of non-malignant cells.

In one aspect, the above-described agents capable of binding microvesicles are immobilized on a porous hollow fiber membrane, e.g., on the porous exterior of the hollow fiber membrane.

In another aspect of the invention, existing methods and devices of extracorporeal treatment of blood are integrated (in whole or in part) for augmenting ex vivo clearance of microvesicles in a physiologically applicable manner. Exemplary existing methods for extracorporeal treatment of blood are selected from one or more of the following: a) hemofiltration; b) hemodialysis; and c) hemodiafiltration. A presently preferred existing method for extracorporeal treatment of blood comprises apheresis followed by filtration.

In accordance with yet another embodiment of the present invention, there are provided methods of enhancing the immune response of a subject in need thereof through the removal of microvesicular particles found in systemic circulation of said subject, said methods comprising:

a) establishing an extracorporeal circulation system which comprises contacting the whole blood or components thereof with a single or plurality of agents capable of binding microvesicles found within said blood or components thereof, said agents being in turn bound to a plurality of objects;

b) performing a filtration step such that said objects of a defined size are captured within said extracorporeal circulation system; and c) returning said blood or components thereof into the subject, said blood or blood components containing substantially less immune suppressive particles in comparison to the blood or blood components originally residing in said subject.

Enhancing immune response contemplated herein includes one or more of the following: upregulation of T cell, natural killer (NK) cell, natural killer T (NKT) cell, gamma-delta T cell, and B cell function. It is presently preferred that upregulation of one or more of T cell, natural killer (NK) cell, natural killer T (NKT) cell gamma-delta T cell, and B cell function includes prevention of apoptosis. It is also presently preferred that upregulation of one or more of T cell, natural killer (NK) cell, natural killer T (NKT) cell gamma-delta T cell, and B cell function includes enhancing and/or endowment of activity capable of inhibiting cancer progression.

Inhibiting cancer progression contemplated herein is accomplished by one or more of the following: direct cytolysis of tumor cells, direct induction of tumor cell apoptosis, induction of tumor cell cytolysis through stimulation of intrinsic host antitumor responses, induction of tumor cell apoptosis through stimulation of intrinsic host antitumor responses, inhibition of tumor cell metastasis, inhibition of tumor cell proliferation, and induction of senescence in the tumor cells.

Tumor cells contemplated for treatment in accordance with the present invention are selected from the group of cancers consisting of: soft tissue sarcomas, kidney, liver, intestinal, rectal, leukemias, lymphomas, and cancers of the brain, esophagus, uterine cervix, bone, lung, endometrium, bladder, breast, larynx, colon/rectum, stomach, ovary, pancreas, adrenal gland and prostate.

Agents capable of binding microvesicles contemplated for use herein are selected from the group consisting of one or more of the following: a) a singular or plurality of antibody species; b) a singular or plurality of proteins (e.g., lectins); c) a singular or plurality of aptamers, d) a surface that selectively restricts microvesicles from passage, and e) a surface with selective adhesion to microvesicles.

The plurality of objects contemplated for use herein comprise beads manufactured to a specific size or range of sizes in a manner so that said agents capable of binding microvesicles may be conjugated to said plurality of objects. Preferably such beads have a defined size range to restrict their movement out of said extracorporeal circulation system, e.g., the beads are of a size range larger than pores of hollow fibers used in extracorporeal systems so as to restrict their movement out of said extracorporeal systems. In one aspect, such beads possess properties responsive to an electromagnetic field, such that subsequent to said beads contacting said microvesicles, said beads may be removed or sequestered by said electromagnetic field in order to substantially prevent movement of said beads out of said extracorporeal system.

Examples of beads contemplated for use herein are MACS™ beads alone or conjugated with compounds in order to allow said beads to form complexes with said agents capable of binding microvesicles, Dynal™ beads alone or conjugated with compounds in order to allow said beads to form complexes with said agents capable of binding microvesicles, and the like.

Antibodies contemplated for use herein have a specificity for proteins selected from a group consisting of one or more of the following: Fas ligand, MHC I, MHC II, CD44, placental alkaline phosphatase, TSG-101, MHC I-peptide complexes, MHC II-peptide complexes, and proteins found to be present on the exterior of microvesicles contributing to immune suppression found in a cancer patient. Presently preferred antibodies are specific to Fas ligand, MHC I, and the like.

Proteins contemplated for use herein are selected from the group consisting of one or more of the following: Fas, T cell Receptor, protein extracts isolated from T cells, protein extracts isolated from dendritic cells, and proteins found to possess affinity for binding proteins found on microvesicles associated with immune suppression.

Surfaces that selectively restrict passage of said microvesicles typically fall in the range of about 20-400 nanometers in size, with microvesicles falling in the range of about 40-300 nanometers in size being presently preferred, and microvesicles in the range of about 50-280 nanometers in size being especially preferred.

Exemplary surfaces with selective adhesion to microvesicles are coated with a single compound, or plurality of compounds that bind particles that are enriched in sphingomyelin and with a lower level of phosphatidylcholine as found in the cellular membranes of non-malignant cells.

In accordance with another aspect of the invention, agents capable of binding microvesicles can be immobilized on a porous hollow fiber membrane, e.g., on the porous exterior of the hollow fiber membrane.

In accordance with still another aspect of the present invention, existing methods and devices of extracorporeal treatment of blood can be integrated (in whole or in part) with the above-described methods to augment ex vivo clearance of microvesicles in a physiologically applicable manner. Exemplary methods contemplated for use herein include: a) hemofiltration; b) hemodialysis; and c) hemodiafiltration, with a preferred method including apheresis followed by filtration.

In accordance with various aspects of the present invention, extracorporeal removal of microvesicles can be performed through selective adhesion of said microvesicles to matrices or substrates that are conjugated to agents possessing higher affinity to microvesicles with a high sugar content, in comparison to microvesicles of a lower sugar content.

In accordance with yet another embodiment of the present invention, there are provided methods of extracorporeally removing microvesicles from a subject in need thereof, said method comprising passing said subject's whole blood, or separated blood components, through a system capable of selectively binding and retaining microvesicles based on one or more of size, charge, affinity towards lectins, or affinity towards molecules that are known to be present on said microvesicles.

In accordance with a further embodiment of the present invention, there are provided methods of extracorporeally removing microvesicles from a subject in need thereof, said methods comprising passing said subject's whole blood, or separated blood components, through a system capable of non-selectively binding and retaining microvesicles based on one or more of size, charge, affinity towards lectins, or affinity towards molecules that are known to be present on said microvesicles.

In accordance with a still further embodiment of the present invention, there are provided methods of extracorporeally removing microvesicles from a subject in need thereof, said methods comprising passing said subject's whole blood, or separated blood components, through a system capable of selectively binding and retaining microvesicles based on similarities between properties of microvesicles and membranes of cancer cells.

In accordance with yet another embodiment of the present invention, there are provided methods of extracorporeally removing microvesicles from a subject in need thereof, said methods comprising passing said subject's whole blood, or separated blood components, through a system capable of non-selectively binding and retaining microvesicles based on similarities between properties of microvesicles and membranes of cancer cells.

When carrying out the above-described methods, the similarities between cancer associated microvesicles and membranes of cancer cells include ability to bind a lectin or plurality of lectins. Reference to lectins herein includes GNA, NPA, Conconavalin A and cyanovirin, with a presently preferred lectin being Conconavalin A.

One embodiment of the present invention relates to methods that can be used for extracorporeal treatment of blood or a blood fraction for the removal of microvesicles associated with immune suppression in a cancer patient. Blood is run through an extracorporeal circulation circuit that uses a hollow fiber cartridge with the membranes of said hollow fibers having sufficient permeability for the microvesicles found in the blood to be removed through the membrane of the hollow fibers and into an area outside of the fibers containing a substrate that is bound to a single or plurality of agents capable of adhering to said microvesicles in a manner such that said microvesicles are attached to said agent and do not substantially re-enter the hollow fibers. Within the knowledge of one skilled in the art are available numerous types of hollow fiber systems. Selection of said hollow fiber system is dependent on the desired blood volume and rate of passage of said blood volume through the hollow fiber system. Specifically, hollow fiber cartridges may be used having lengths of 250 mm and containing 535 hollow fibers supplied by Amicon, and having the fiber dimensions: I.D. 180 micron and O.D. 360 micron, and the total contact surface area in the cartridge is 750 cm$^2$. Alternatively, the "Plasmaflux P2" hollow fiber filter cartridge (sold by Fresenius) or Plasmart PS60 cartridges (sold by Medical srl) may be used. These and other hollow fiber systems are described by Ambrus and Horvath in U.S. Pat. No. 4,714,556 and incorporated herein by reference in its entirety. Hollow fiber cartridges such as described by Tullis in United States Patent Application 20040175291 (incorporated by reference herein in its entirety) may also be used. Furthermore, said hollow fiber cartridges and affinity cartridges in general are thought in U.S. Pat. Nos. 4,714,556, 4,787,974 and 6,528,057, which are incorporated herein by reference in their entirety.

Regardless of hollow fiber system used, the concept needed for application of the present invention, is that said hollow fiber filters are required to allow passage of blood cells through the interior of said hollow fiber, and allow diffusion of microvesicles to the exterior. In order to allow such diffusion, the pores on the membrane of the hollow fiber need to be of a diameter sufficient to allow particles ranging from the size of 20 nanometers to 500 nanometers in diameter. More specifically, the pores on the membrane of the hollow fiber need to be of a diameter sufficient to allow particles ranging from the size of 50 nanometers to 300 nanometers in diameter. Even more specifically, the pores on the membrane of the hollow fiber need to be of a diameter sufficient to allow particles ranging from the size of 80 nanometers to 200 nanometers in diameter. During experimentation with different hollow fibers, one skilled in the art would find it useful to utilize particles of similar size ranges as the microvesicles in order to calibrate and quantitate the ability of various pore sizes of hollow filters. One method of performing this is through the utilization of commercially available MACS™ Beads (Milteny Biotech), which have a size of 60 nanometers. Fluorescent, spherical latex beads ranging in size from 25 to 1000 nm are also available for this purpose (e.g., from Duke Scientific (Palo Alto, Calif.)).

The substrate or matrix to be used in practicing the present invention needs to allow sufficient permeation of flow so that non-cellular blood components that enter the space exterior to the hollow fiber are distributed throughout the substrate or matrix material, so that substantial contact is made between the microvesicles permeating the hollow fiber filter and the microvesicle-binding agent that is attached to the substrate or matrix. Suitable substrates or matrices are known to one skilled in the art. Said substrates or matrices include silica gel, dextran, agarose, nylon polymers, polymers of acrylic acid, co-polymers of ethylene and maleic acid anhydride, aminopropylsilica, aminocelite, glass beads, silicate containing diatomaceous earth or other substrates or matrices known in the art. Examples of such are described in the following patents, each of which are incorporated by reference herein in their entirety: Lentz U.S. Pat. No. 4,708,713, Motomura U.S. Pat. No. 5,667,684, Takashima et al U.S. Pat. No. 5,041,079, and Porath and Janson U.S. Pat. No. 3,925,152. The agents that are attached to said substrate are chosen based on known affinity to cancer associated microvesicles. Said agents may be capable of non-specifically binding to said microvesicles, in that binding occurs both from non-tumor associated microvesicles, and from tumor associated microvesicles, or conversely, said agents may display a certain degree of selectivity for exosomes derived from tumors.

In one embodiment said agents non-specifically bind all microvesicles due to common expression of molecules such as MHC I on microvesicles that are associated with conditions of neoplasia, and microvesicles that are not. Specifically, an agent that would bind both types of microvesicles would be an antibody specific to the non-polymorphic regions of MHC I. Therefore, in the embodiment of the invention in which non-selective removal of microvesicles is sought, anti-MHC I antibodies would be bound to said substrate chosen, and the combination would be placed to reside outside of the hollow fiber filters in order to allow binding of said microvesicles to the substrate, however blood cells and other components of the blood would not be removed during the passage of blood through the encased system containing said hollow fiber filters, exterior substrate, and microvesicle binding agent.

In order to achieve non-specific removal of microvesicles, another embodiment of the invention is the use of hollow fiber filters of sufficient size of the pores on the side of the hollow fiber filter for microvesicles to exit, while not allowing blood cells to exit, and passing a continuous solution over said hollow fiber filters in order to clear said microvesicles leaking through the sides of the hollow fiber filters. In such a situation it would be critical to re-introduce the other blood components that escaped the hollow fiber filter, such as albumin, back into the microvesicle purified blood, before returning of the blood to the subject.

Alternatively, the hollow-fiber cartridge may be sealed as described in Ambrus. In such a system, both diffusion and convection cause blood fluids (exclusive of blood cells) to pass through the pores in the hollow fibers and into contact with the capture molecules bound to the solid phase matrix. The fluids (e.g. plasma) pass back into the circulation at the distal end of the cartridge through a process known as Starling flow. In this system, there is no significant loss of blood fluids and therefore no need for blood component replacement.

In the situations where a substantially specific removal of microvesicles associated with tumors is desired, the said agent bound to said substrate outside of said hollow fiber filters possesses affinity to molecules specifically found on said microvesicles associated with tumors. Said agent may be an antibody to the molecule Fas Ligand, may be a recombinant Fas protein, or may be directed to MHC I, MHC II, CD44, placental alkaline phosphatase, TSG-101, MHC I-peptide complexes, MHC II-peptide complexes, and proteins found to be present on the exterior of microvesicles contributing to immune suppression found in a cancer patient. Another embodiment of the invention takes advantage of the similarity of tumor membranes with tumor microvesicles and the known high concentration of mannose and other sugars on tumor membranes compared to membranes of non-malignant cells.

In a situation where microvesicles associated with tumors are meant to be withdrawn with a certain degree of selectivity from the systemic circulation of a subject in need thereof, said agent binding the matrix or substrate may be a lectin. Specific methodologies for use of lectins in removal of viruses are described by Tullis in United States Patent Application 20040175291 (incorporated by reference herein in its entirety) and these methodologies may also be used in part or in whole for practicing the present invention. In various embodiments of the invention, it is important that said systems include means for maintaining the blood at conditions similar to that found in the host, so that upon returning said blood to the host, no adverse reactions occur. In other words, it is within the scope of the invention to use technologies that are known to one skilled in the art to maintain blood at physiological ion concentrations, osmolality, pH, hematocrit, temperature, and flow in order to avoid harm being caused to the subject subsequent to reinfusion of blood treated as disclosed herein. Said technologies are well known to one skilled in the art.

In another embodiment of the invention a system for extracorporeal clearance of microvesicles; either selectively removing tumor associated microvesicles, or non-selectively microvesicles that are found in healthy subjects as well as tumor bearing subjects. The invention comprises several interacting components whose primary purpose is the formation of a functional circuit capable of depleting microvesicles in order to de-repress, or in some cases augment the immune response of a cancer patient. More specifically, a means for separating blood from a subject in need thereof (e.g., a cancer patient) into plasma and cellular elements is used. Appropriate means for such separation are available commercially, and well-known to the skilled artisan. They include, for example, the Exorim System, the Fresenius Hemocare Apheresis system, and the Gambo Prisma System. Plasma purified through said separation means is then run over an array of filtration means, said filtration means possessing a higher affinity towards tumor associated microvesicles in comparison to other molecules. Said filtration means includes, in some embodiments, microvesicle binding agents immobilized to a substrate.

Said microvesicle binding agents include but are not limited to antibodies, proteins, or compounds with selective affinity towards microvesicles associated with the cancer or not associated. Examples of such agents include antibodies to Fas ligand, MHC I, MHC II, CD44, placental alkaline phosphatase, TSG-101, MHC I-peptide complexes, MHC II-peptide complexes, or proteins found to be present on the exterior of microvesicles contributing to immune suppression found in a cancer patient, as well as lectins such as conconavalin A, phytohemagluttanin, GNA, NPA, and cyanovirin. Said substrate is selected from known substrates previously used in the are, these include, for example SEPHAROSE™ made by Amersham-Biosciences, Upsala, Sweden, as well as acrylamide and agarose particles or beads. The substrates used should have the properties of being able to tightly bind the microvesicle binding agent, the ability to be produced in a sterile means, and be compatible with standard dialysis/extracorporeal tubings.

In other embodiments, the agent capable of binding the tumor associated or non-tumor associated microvesicles is immobilized to a filter membrane or capillary dialysis tubing, where the plasma passes adjacent to, or through, the membranes to which said agent capable of binding the tumor associated or non-tumor associated microvesicles are bound. Suitable filters include those mentioned previously with respect to separation of blood components. These may be the same filters, having immobilized agents capable of binding microvesicles (either tumor associated or non-associated, or may be arranged in sequence, so that the first filter divides the blood components and the secondary, tertiary and additional filter removes one or more of the components of said cancer associated microvesicles. Conjugation of the agent capable of binding the tumor associated or non-associated microvesicle to said substrate may be accomplished by numerous means known in the art. Said means include avidin-streptavidin, cynanogen bromide coupling, the use of a linker such as a polyethylene glycol linker. A means of returning the blood together with plasma substantially cleared of tumor associated microvesicles back to said subject is also provided in the invention. Preferred means are chosen by one of skill in the art based on the desired application, extent of microvesicle removal desired, patient condition, extracorporeal method chosen, and microvesicle-binding agent chosen.

In one embodiment of the invention, extracorporeal removal of microvesicles is performed in a cancer patient in order to accelerate the rate of tumor-specific T cell proliferation and activation. It is known in the art that tumors contain antigens that are specific to the tumor (e.g. the bcr-abl product p210 in CML), expressed on other tissues but overexpressed on cancer cells (e.g. tyrosinase), or expressed embryonically and re-expressed in the cancer (e.g. telomerase). Vaccination to such antigens has been demonstrated to induce immune response, and in some cases generation of cytotoxic T lymphocytes (CTL). Unfortunately, despite much effort in development of cancer vaccines, clinical translation has been slow, with most cancer vaccines not demonstrating efficacy in the double-blind setting. In order to increase efficacy of cancer vaccines, it is important that the cancer patient has an immunological environment in which proper T cell activation may occur. It is known that high numbers of microvesicles are present in the circulation of patients with a wide variety of histologically differing tumors including melanoma (52), ovarian (53), colorectal (54), and breast (55). Importantly, such microvesicles are known to induce suppression of immunity via direct mechanisms such as induction of T cell death via FasL expression (52), through indirect mechanisms such as stimulation of myeloid suppressor cell activity (54).

Indeed, numerous mechanisms are known for suppression of T cell immunity by cancer-secreted microvesicles (56-59). Accordingly, in one embodiment a cancer patient is treated with a therapeutic cancer vaccine either prior to, concurrently, or subsequent to undergoing extracorporeal removal of exosomes. Said cancer vaccine may be used for stimulation of immune responses to antigens that are found either exclusively on the tumor, to antigens found on non-malignant tissues but at higher concentration on the tumor, or antigens whose presence is required for tumor functionality. In a specific embodiment of the invention, tumor vaccination is performed to peptides, polypeptides, glycoproteins, peptidomimetics, or combinations thereof. Tumor vaccination may be performed in the context of a cell therapy, such as, for example, administration of dendritic cells that are pulsed with tumor antigens or tumor lysates. Tumor vaccines are commonly known in the art and are described in the following reviews, which are incorporated by reference (60-64). Examples of tumor antigens that may be used in the practice of the current invention include CDK-4/ma MUM-1/2, MUM-3, Myosin/m, Redox-perox/m, MART-2/m, Actin/4/ma, ELF2-M, CASP-8/ma, HLA-A2-R17OJ, HSP70-2/ma, CDKN2A, CDC7a, TPI, LDLR/FUT Fibronectin/m, RT-PTP-K/ma, BAGE, GAGE, MAGE, telomerase, and tyrosinase, and fragments thereof.

In one specific embodiment, a patient with ovarian cancer is selected for treatment with cancer vaccination. Said patient plasma is assessed for exosomal content based on methods known in the art, as for example described in the following study and incorporated herein by reference (65). In specific method involves the following procedure: ETDA treated plasma is purified from peripheral blood by centrifugation at 500 g for half-hour. Separation of cellular debris is accomplished by a second centrifugation at 7,000 g for an additional half-hour. Exosomes are subsequently collected by centrifugation at 100,000 g for 3 hours, followed by a washing step in PBS under the same conditions. Using this procedure, approximately 0.5-0.6 ug/ml of exosomal protein is detected from healthy volunteers as visualized by the Bradfort Assay (Bio-Rad, Hercules, Calif.) (66). In contrast, the plasma of cancer patients typically contains a higher exosomal yield, ranging between 200-500 ug/ml. This is in agreement with studies describing high concentrations of "membrane vesicles" found systemically circulating in cancer patients (65). For the practice of the invention patients with high exosomal content compared to healthy volunteers are selected. For example, patients with exosomal content above two fold the concentration of exosomes in healthy volunteers may be treated by the invention. In another embodiment, patients with exosomal contented 10-fold higher than exosomal content of healthy volunteers are treated. In another embodiment of the invention, patients with higher exosomal content than healthy volunteers which have spontaneous T cell apoptosis present are selected for treatment. Protocols for assessment of spontaneous T cell apoptosis are known in the art and described, for example by Whiteside's group and incorporated here by reference (67). Assessment of exosome immune suppressive activity may be quantified by culture of exosomes purified from patient plasma with a Fas expressing T cell line such as the Jurkat clone E6.1 (ATCC Manassas, Va.). These cells may be cultured in standard conditions using the method described by Andreola et al and incorporated herein by reference (52) in order to develop a standardized assay. Briefly $10^6$/ml Jurkat cells are seeded in 24-well plates in 10% FBS RPMI 1640 and co-cultured with escalating concentrations of exosomes from healthy volunteers, as well as cancer patients. Apoptosis of Jurkat cells may be quantified by assessment of Annexin-V staining using flow cytometry.

Patients displaying elevated numbers of exosomes, and/or apoptotic T cells, and/or possessing exosomes capable of inducing T cell apoptosis are selected for extracorporeal removal of said exosomes. In one preferred embodiment, patent blood is passaged over an extracorporeal circuit for a time sufficient to substantially reduce exosome burden. Reduction of exosome burden is quantified as described above. Correlation can be made between exosome concentration and spontaneous T cell apoptosis. When reduction of both plasma exosome concentration and spontaneous T cell apoptosis is achieved, said patient may be immunized with a tumor vaccine. Alternatively, patients may have exosome removal performed without immunization with a tumor vaccine so as to allow for endogenous antitumor responses to be derepressed. Alternatively patients may be treated with a non-specific immune stimulator, said immune stimulator may be a small molecule (e.g. muramyl dipeptide, thymosin, 7,8-disubstituted guanosine, imiquimod, detoxified lipopolysaccharide, isatoribine or alpha-galactosylceramide), a protein (e.g. IL-2, IL-7, IL-8, IL-12, IL-15, IL-18, IL-21, IL-23, IFN-a, b, g, TRANCE, TAG-7, CEL-1000, bacterial cell wall complexes, or LIGHT), or an immunogeneic nucleic acid (e.g. short interfering RNA targeting the mRNA of immune suppressive proteins, CpG oligonucleotides, Poly IC, unmethylated oligonucleotides, plasmid encoding immune stimulatory molecules, or chromatin-purified DNA). Said non-specific immune stimulants are known in the art and in some cases are already in clinical use. Said non-specific immune stimulants in clinical use include interleukin-2, interferon gamma, interferon alpha, BCG, or low dose cyclophosphamide.

In another embodiment extracorporeal removal of exosomes is performed in conjunction with chemotherapy in order to derepress immune suppression caused by exosomes, while at the same time allowing said chemotherapy to perform direct tumor inhibitory functions. Alternatively, extracorporeal removal of exosomes may be utilized to remove increased exosomes caused by tumor cell death during chemotherapy use. Numerous types of chemotherapies are known in the art that may be utilized in the context of the present invention, these include: alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylolomelamine; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenishes such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL®, Bristol-Myers Squibb Oncology, Princeton, N.J.) and docetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; and capecitabine.

In one embodiment, frequency and length of extracorporeal treatment is performed based on the amount of time (or blood volume) needed for reduction of exosome concentration to a level significant to correlate with reduction in spontaneous T cell apoptosis. In one embodiment a reduction of spontaneous T cell apoptosis by approximately 20% in comparison to pre-extracorporeal treatment values is judged as sufficient. In another embodiment a reduction of spontaneous T cell apoptosis by approximately 50% in comparison to pre-extracorporeal treatment values is judged as sufficient. In another embodiment a reduction of spontaneous T cell apoptosis by approximately 90% in comparison to pre-extracorporeal treatment values is judged as sufficient.

Although assessment of spontaneous T cell apoptosis is used in some embodiments for judging the frequency, and/or time, and/or blood volume needed for extracorporeal treatment, other means of measuring immune responses may be used. For example restoration of cytokine production (68), T cell proliferation (69), or TCR-zeta chain expression (70) are all known in the art and described in the references incorporated herein.

One skilled in the art will appreciate that these methods and devices are and may be adapted to carry out the objects and obtain the ends and advantages mentioned, as well as those inherent therein. The methods, procedures, and devices described herein are presently representative of preferred embodiments and are exemplary and are not intended as limitations on the scope of the invention. Changes therein and other uses will occur to those skilled in the art which are encompassed within the spirit of the invention and are defined by the scope of the disclosure. It will be apparent to one skilled in the art that varying substitutions and modifications may be made to the invention disclosed herein without departing from the scope and spirit of the invention.

EXAMPLES

There are numerous methods of conjugating antibodies to substrates that are used for packing the Hollow Fiber Cartridge. In the examples, the binding of proteins and other chemical binding agents is generally performed using variations of the glutaraldehyde techniques described by Ambrus and Horvath in U.S. Pat. No. 4,714,556 (incorporated herein by reference in its entirety).

Example 1

Preparation of GNA Covalently Coupled to Agarose Using Cyanogen Bromide

Cyanogen bromide (CNBr) activated agarose was used for direct coupling essentially according to Cuatrecasas, et al (Cuatracasas, Wilchek and Anfinsen. Proc Natl Acad Sci USA 61(2): 636-643, 1968). In brief, 1 ml of GNA at a concentration of 10 mg/ml in 0.1M $NaHCO_3$ pH 9.5 is added to 1 ml CNBr activated agarose (Sigma, St. Louis, Mo.) and allowed to react overnight in the cold. Care must be taken to maintain alkaline pH to prevent the potential release of HCN gas. When the reaction is complete, unreacted materials are aspirated and the lectin coupled agarose washed extensively with sterile cold PBS. The lectin agarose affinity matrix is then stored cold until ready for use. Alternatively, GNA agarose is available commercially from Vector Labs (Burlingame, Calif.)

Example 2

Preparation of an Antibody Covalently Coupled to Glass Beads Via Schiff's Base and Reduction with Cyanoborohydride The affinity matrix was prepared by a modification of the method of Hermanson (Hermanson. Bioconjugate Techniques: 785, 1996). Anti-HIV monoclonal antibody dissolved to a final protein concentration of 10 mg/ml in 0.1M sodium borate pH 9.5 is added to aldehyde derivatized silica glass beads (BioConnexant, Austin Tex.). The reaction is most efficient at alkaline pH but will go at pH 7-9 and is normally done at a 2-4 fold excess of protein over coupling sites. To this mixture is added 10 ul 5M $NaCNBH_3$ in 1N NaOH (Aldrich, St Louis, Mo.) per ml of coupling reaction and the mixture allowed to react for 2 hours at room temperature. At the end of the reaction, remaining unreacted aldehyde on the glass surfaces are capped with 20 ul 3M ethanolamine pH 9.5 per ml of reaction. After 15 minutes at room temperature, the reaction solution is decanted and the unbound proteins and reagents removed by washing extensively in PBS. The matrix is the stored in the refrigerator until ready for use.

Example 3

Preparation of an Exosome Specific Antibody Covalently Coupled to Chromosorb (Diatomaceous Earth) Using Glutaraldehyde Preparation of aminated diatomaceous earth is accomplished using γ-aminopropyl triethoxysilane (GAPS) (Sigma Chemical, St. Louis, Mo.) and Chromosorb 60/80 mesh. Although other grades of diatomaceous earth may be used, Chromosorb of this mesh size (200-300 microns in diameter) is often used to prevent small particulates from entering the sample through the largest available pore sizes found in hollow-fiber cartridges used for plasma separation (~0.5 micron).

Amino Chromosorb was prepared by suspension in an excess of 5% aqueous solution of GAPS in an overnight reaction. Aminated-Chromosorb was washed free of excess reagent with water and ethanol and dried overnight in a drying oven to yield an off white powder. One gram of the powder was then suspended in 5 ml 5% glutaraldehyde (Sigma) for 30 minutes. Excess glutaraldehyde was then removed by filtration and washing with water until no detectable aldehyde remained in the wash using Schiff's reagent (Sigma Chemical). The filter cake was then resuspended in 5 ml of Sigma borohydride coupling buffer containing 2-3 mg/ml of the antibody and the reaction allowed to proceed overnight at 4 degrees C. At the end of the reaction, excess antibody is washed off and the remaining aldehyde reacted with ethanolamine as described. After final washing in sterile PBS, the material was stored cold until ready for use.

Example 4

Preparation of an AntiFas-Ligand Specific Antibody Covalently Coupled to Polyacrylate Beads Using Glutaraldehyde and Azide Anti-Fas Ligand antibody (NOK-1 mouse anti-human as described by Kayagaki et al in U.S. Pat. No. 6,946,255 and incorporated herein by reference in its entirety) is dissolved in a concentration of 50-200 mg./ml. with human serum albumin in a phosphate-buffered aqueous medium of pH 7.0. Glutaraldehyde at a concentration of 0.05-10% is added to the solution which is then incubated for 1-24 hours, but preferably 12 hours, at 4.degree. C. Excess glutaraldehyde that remains in the reaction mixture is removed by addition of glycine, or other suitable compounds known in the art, to the solution at the end of incubation. This solution is then diafiltered through a membrane having a minimal retentively value of 500,000 molecular weight. The diafiltered antibody-bearing product is dissolved in saline or dialysis fluid. To obtain a reactive polymer to act as a substrate for said anti-Fas Ligand antibody, polyacrylic acid polymer beads (micron in diameter) are activated by the azide procedure (51). The ratios of antibody to reactive polyester are selected to avoid excessive reaction. If this ratio is appropriately adjusted, the spacing of the antibody along the polymer chain will allow a binding of the antibody with the antigen found on microvesicle without untoward steric hindrances and the antibody conjugate is intended to remain soluble.

Said antiFas Ligand antibody conjugates are subsequently loaded into a hollow fiber filter cartridge, on the exterior of said hollow fibers. The external filling ports are then sealed. This allows for passage of blood cell components through the lumen of said hollow fibers. Blood plasma containing the microvessicles, convects and diffuses through pores in the hollow fibers into the extralumenal space where it contacts the antibody-polyacrylate conjugates. Treated plasma inside the cartridge diffuses back into the general circulation leaving the microvesicles attached to the insolublized anti-FAS Ligand antibody.

Example 5

Patient Treatment Using AntiFas-Ligand Specific Antibody Covalently Coupled to Polyacrylate Beads from Example 4

A patient with stage IV unresectable colorectal cancer presents with a suppressed ability to produce interferon-gamma subsequent to ex vivo stimulation of peripheral blood mononuclear cells with anti-CD3. In order to de-repress the ability of said patients immune response to produce interferon gamma, said patient is treated with an extracorporeal device capable of removing microvesicles that contribute, at least in part, to the suppressed production of interferon gamma. Said medical device is manufactured as in Example 4:

The modified hollow fiber filter is connected to a venovenous dialysis machine and connected to the circulation of said patient for a time period necessary to remove microvesicles associated with suppression of interferon gamma production. Vascular access is obtained via a double-lumen catheter in the subclavian or femoral vein. For this specific application the hollow fiber hemofilter is connected to a flow-controlled blood roller pump, the blood flow rate ($Q_b$) is set at 100 to 400 ml/min, (more preferably at 200 to 300 ml/min depending on the cardiovascular stability of the patient). The dialysis circuit is anticoagulated with a continuous heparin infusion in the afferent limb. The activated clotting time (ACT) is measured every hour, and the heparin infusion is adjusted to maintain the ACT between 160 and 180 seconds. Said patient is monitored based on the concentration of microvesicles expressing Fas Ligand in circulation, as well as by ability of said patient lymphocytes to produce interferon gamma in response to mitogenic or antibody stimulation.

Upon upregulation of interferon gamma production, said patient can be administered a tumor vaccine with the goal of antigen-specifically stimulating host immune responses in an environment conducive to immune-mediated clearance of the primary and/or metastatic tumors.

Example 6

Removal of Exosomes from Blood Using Plasmapheresis

Selective removal of exosomes from blood may be accomplished using plasmapheresis combined with affinity capture using any of the matrices described in Examples 1-5. Plasmapheresis is done using either centrifugal separation or hollow-fiber plasma separation methods. The blood circuit is anticoagulated with a continuous heparin infusion in the afferent limb. The activated clotting time (ACT) is measured every hour, and the heparin infusion is adjusted to maintain the ACT between 160 and 180 seconds.

The plasma obtained from the patient may be discarded and replaced with a combination of normal saline and fresh plasma from healthy donors (i.e. plasma exchange). Alternatively, the plasma containing the microvesicles can be pumped at 60-100 ml/min over the affinity matrix which captures the exosomes. The cleaned plasma may then be reinfused into the patient. A similar system (the Prosorba column) has been described for the removal of immunoglobulin complexes from patients with drug refractory rheumatoid arthritis (71, 72). The clearance of the microvesicles may be monitored based on the concentration of microvesicles expressing Fas Ligand remaining in circulation.

Example 7

Direct Coupling of an Aptamer Specific for Tumor Exosomes to the Hollow-Fibers

In hollow-fiber based devices, more intimate contact with the blood is obtained by direct coupling of the capture agent to the hollow-fibers. Aptamers are short pieces of synthetic DNA and its chemical derivatives which bind to specific antigens (i.e. DNA antibodies). The process for generating aptamers is described in detail in U.S. Pat. No. 5,567,588 (1996; issued to Gold et al.; incorporated herein by reference in its entirety). In this example the isolation of Fas Ligand protein specific DNA aptamers and the production of hollow-fiber coupled aptamer affinity matrices are described. Purified Fas Ligand protein is chemically coupled to agarose using Amino-Link agarose (Pierce Chemical Co.). AminoLink Coupling Gel is a 4% crosslinked beaded agarose support, activated to form aldehyde functional groups which develops a stable bond, in the form of a secondary amine, between the gel and the protein with coupling efficiencies of 85% between pH 4-10. In this example 2 ml Fas Ligand protein (1 mg/ml in coupling buffer) is applied to the Aminolink gel for 7 hours at 4 degrees C. Unreacted protein is then washed off with 25 volumes of phosphate buffered saline (PBS) and the product material stored cold until ready for use.

Next DNA oligonucleotides, typically 80 nucleotides long are prepared containing the following elements. First a PCR primer site of 20 nucleotides on both the 5' and 3' ends and a 40 base segment in the middle of the molecule prepared with a random mixture of bases. This generates a very large number of DNA species from which the specific aptamer (i.e. DNA antibody) may be selected. The DNA capable of binding selectively to the target protein Fas Ligand is then selected by multiple rounds of binding to the immobilized Fas Ligand interspersed with polymerase chain reaction (PCR) amplification on the recovered fragments. The final material with high selectivity for Fas Ligand may then be cloned and sequenced to yield a consensus sequence. Copies of the consensus sequence are then chemically synthesized with 5' or 3' terminal amino groups and coupled to a solid phase such as described in Example 3.

In this specific example, the chemically synthesized FasL specific aptamer containing a terminal amine is to be coupled directly to polysulfone hollow-fibers in situ in a plasma separator cartridge. To accomplish this, the cartridge is first exposed to a solution of 4% human serum albumin (HSA) reacted overnight at 4 degrees C. The adsorbed HSA is then cross-linked with glutaraldehyde. Excess glutaraldehyde is then briefly washed out with water. The cartridge is then filled with Sigma cyanoborohydride coupling buffer containing 2-3 mg/ml of the aminated FasL aptamer and reacted overnight at 4 degrees C. At the end of the reaction, excess aptamer is washed off and the remaining unreacted aldehyde reacted with ethanolamine. After final washing in sterile PBS, the cartridge was dried in sterile air, packaged and sterilized using gamma-irradiation (25-40 kGy) and stored in a cool, dark area until ready for use.

Those skilled in the art recognize that the aspects and embodiments of the invention set forth herein may be practiced separate from each other or in conjunction with each other. Therefore, combinations of separate embodiments are within the scope of the invention as disclosed herein. All patents and publications mentioned in the specification are indicative of the levels of those skilled in the art to which the invention pertains. All patents and publications are herein incorporated by reference to the same extent as if each individual publication was specifically and individually indicated to be incorporated by reference. The invention illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions indicates the exclusion of equivalents of the features shown and described or portions thereof. It is recognized that various modifications are possible within the scope of the present invention. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the disclosure.

REFERENCES

1. Wiemann, B., and Starnes, C. O. 1994. Coley's toxins, tumor necrosis factor and cancer research: a historical perspective. *Pharmacol Ther* 64:529-564.
2. Woglom, W. 1929. *Cancer Rev.* 4:129.
3. Ichim, C. V. 2005. Revisiting immunosurveillance and immunostimulation: Implications for cancer immunotherapy. *J Transl Med* 3:8.
4. Romagnani, S. 1992. Human TH1 and TH2 subsets: regulation of differentiation and role in protection and immunopathology. *Int Arch Allergy Immunol* 98:279-285.
5. Sanders, V. M. 2005. Epigenetic regulation of Th1 and Th2 cell development. *Brain Behav Immun.*
6. Zhu, J., Yamane, H., Cote-Sierra, J., Guo, L., and Paul, W. E. 2006. GATA-3 promotes Th2 responses through three different mechanisms: induction of Th2 cytokine production, selective growth of Th2 cells and inhibition of Th1 cell-specific factors. *Cell Res* 16:3-10.
7. Curiel, R. E., Lahesmaa, R., Subleski, J., Cippitelli, M., Kirken, R. A., Young, H. A., and Ghosh, P. 1997. Identification of a Stat-6-responsive element in the promoter of the human interleukin-4 gene. *Eur J Immunol* 27:1982-1987.
8. Lederer, J. A., Perez, V. L., DesRoches, L., Kim, S. M., Abbas, A. K., and Lichtman, A. H. 1996. Cytokine transcriptional events during helper T cell subset differentiation. *J Exp Med* 184:397-406.
9. Szabo, S. J., Kim, S. T., Costa, G. L., Zhang, X., Fathman, C. G., and Glimcher, L. H. 2000. A novel transcription factor, T-bet, directs Th1 lineage commitment. *Cell* 100:655-669.
10. Murphy, K. M., Ouyang, W., Szabo, S. J., Jacobson, N. G., Guler, M. L., Gorham, J. D., Gubler, U., and Murphy, T. L. 1999. T helper differentiation proceeds through Stat1-dependent, Stat4-dependent and Stat4-independent phases. *Curr Top Microbial Immunol* 238:13-26.
11. Kacha, A. K., Fallarino, F., Markiewicz, M. A., and Gajewski, T. F. 2000. Cutting edge: spontaneous rejection of poorly immunogenic P1.HTR tumors by Stat6-deficient mice. *J Immunol* 165:6024-6028.
12. Ostrand-Rosenberg, S., Grusby, M. J., and Clements, V. K. 2000. Cutting edge: STAT6-deficient mice have enhanced tumor immunity to primary and metastatic mammary carcinoma. *J Immunol* 165:6015-6019.
13. Ostrand-Rosenberg, S., Clements, V. K., Terabe, M., Park, J. M., Berzofsky, J. A., and Dissanayake, S. K. 2002. Resistance to metastatic disease in STAT6-deficient mice requires hemopoietic and nonhemopoietic cells and is IFN-gamma dependent. *J Immunol* 169:5796-5804.
14. Zhang, S. S., Welte, T., and Fu, X. Y. 2001. Dysfunction of Stat4 leads to accelerated incidence of chemical-induced thymic lymphomas in mice. *Exp Mol Pathol* 70:231-238.
15. Kobayashi, N. 1985. Malignant neoplasms in registered cases of primary immunodeficiency syndrome. *Jpn J Clin Oncol* 15 Suppl 1:307-312.
16. Nakamura, E., Megumi, Y., Kobayashi, T., Kamoto, T., Ishitoya, S., Terachi, T., Tachibana, M., Matsushiro, H., Habuchi, T., Kakehi, Y., et al. 2002. Genetic polymorphisms of the interleukin-4 receptor alpha gene are associated with an increasing risk and a poor prognosis of sporadic renal cell carcinoma in a Japanese population. *Clin Cancer Res* 8:2620-2625.
17. Amirzargar, A., Lessanpezeshki, M., Fathi, A., Amirzargar, M., Khosravi, F., Ansaripour, B., and Nikbin, B. 2005. TH1/TH2 cytokine analysis in Iranian renal transplant recipients. *Transplant Proc* 37:2985-2987.
18. Daniel, V., Naujokat, C., Sadeghi, M., Wiesel, M., Hergesell, O., and Opelz, G. 2005. Association of circulating interleukin (IL)-12- and IL-10-producing dendritic cells with time posttransplant, dose of immunosuppression, and plasma cytokines in renal-transplant recipients. *Transplantation* 79:1498-1506.
19. Kim, W. U., Cho, M. L., Kim, S. I., Yoo, W. H., Lee, S. S., Joo, Y. S., Min, J. K., Hong, Y. S., Lee, S. H., Park, S. H., et al. 2000. Divergent effect of cyclosporine on Th1/Th2 type cytokines in patients with severe, refractory rheumatoid arthritis. *J Rheumatol* 27:324-331.
20. Gerlini, G., Romagnoli, P., and Pimpinelli, N. 2005. Skin cancer and immunosuppression. *Crit Rev Oncol Hematol* 56:127-136.
21. Pluygers, E., Sadowska, A., Chyczewski, L., Niklinski, J., Niklinska, W., and Chyczewska, E. 2001. The impact of immune responses on lung cancer and the development of new treatment modalities. *Lung Cancer* 34 Suppl 2:S71-77.
22. Birkeland, S. A., Storm, H. H., Lamm, L. U., Barlow, L., Blohme, I., Forsberg, B., Eklund, B., Fjeldborg, O., Friedberg, M., Frodin, L., et al. 1995. Cancer risk after renal transplantation in the Nordic countries, 1964-1986. *Int J Cancer* 60:183-189.
23. Khauli, R. B. 1994. Genitourinary malignancies in organ transplant recipients. *Semin Urol* 12:224-232.
24. Penn, I. 1994. Depressed immunity and the development of cancer. *Cancer Detect Prev* 18:241-252.
25. Penn, I. 1994. Occurrence of cancers in immunosuppressed organ transplant recipients. *Clin Transpl:* 99-109.
26. Grulich, A. E., Wan, X., Law, M. G., Coates, M., and Kaldor, J. M. 1999. Risk of cancer in people with AIDS. *Aids* 13:839-843.
27. Marchand, M., van Baren, N., Weynants, P., Brichard, V., Dreno, B., Tessier, M. H., Rankin, E., Parmiani, G., Arienti, F., Humblet, Y., et al. 1999. Tumor regressions observed in patients with metastatic melanoma treated with an antigenic peptide encoded by gene MAGE-3 and presented by HLA-A1. *Int J Cancer* 80:219-230.
28. Liu, M. A., and Ulmer, J. B. 2005. Human clinical trials of plasmid DNA vaccines. *Adv Genet* 55:25-40.
29. Wang, H. H., Mao, C. Y., Teng, L. S., and Cao, J. 2006. Recent advances in heat shock protein-based cancer vaccines. *Hepatobiliary Pancreat Dis Int* 5:22-27.
30. Facciponte, J. G., MacDonald, I. J., Wang, X. Y., Kim, H., Manjili, M. H., and Subjeck, J. R. 2005. Heat shock proteins and scavenger receptors: role in adaptive immune responses. *Immunol Invest* 34:325-342.
31. Garcia-Hernandez, E., Gonzalez-Sanchez, J. L., Andrade-Manzano, A., Contreras, M. L., Padilla, S., Guzman, C. C., Jimenez, R., Reyes, L., Morosoli, G., Verde, M. L., et al. 2006. Regression of papilloma high-grade lesions (CIN 2 and CIN 3) is stimulated by therapeutic vaccination with MVA E2 recombinant vaccine. *Cancer Gene Ther.*
32. Garnett, C. T., Greiner, J. W., Tsang, K. Y., Kudo-Saito, C., Grosenbach, D. W., Chakraborty, M., Gulley, J. L., Arlen, P. M., Schlom, J., and Hodge, J. W. 2006. TRICOM vector based cancer vaccines. *Curr Pharm Des* 12:351-361.

33. Mackensen, A., Herbst, B., Chen, J. L., Kohler, G., Noppen, C., Herr, W., Spagnoli, G. C., Cerundolo, V., and Lindemann, A. 2000. Phase I study in melanoma patients of a vaccine with peptide-pulsed dendritic cells generated in vitro from CD34(+) hematopoietic progenitor cells. *Int J Cancer* 86:385-392.

34. Loveland, B. E., Zhao, A., White, S., Gan, H., Hamilton, K., Xing, P. X., Pietersz, G. A., Apostolopoulos, V., Vaughan, H., Karanikas, V., et al. 2006. Mannan-MUC1-pulsed dendritic cell immunotherapy: a phase I trial in patients with adenocarcinoma. *Clin Cancer Res* 12:869-877.

35. Mu, L. J., Kyte, J. A., Kvalheim, G., Aamdal, S., Dueland, S., Hauser, M., Hammerstad, H., Waehre, H., Raabe, N., and Gaudernack, G. 2005. Immunotherapy with allotumour mRNA-transfected dendritic cells in androgen-resistant prostate cancer patients. *Br J Cancer* 93:749-756.

36. Huang, J., Khong, H. T., Dudley, M. E., El-Gamil, M., Li, Y. F., Rosenberg, S. A., and Robbins, P. F. 2005. Survival, persistence, and progressive differentiation of adoptively transferred tumor-reactive T cells associated with tumor regression. *J Immunother* 28:258-267.

37. Sjogren, H. O., Hellstrom, I., Bansal, S. C., Warner, G. A., and Hellstrom, K. E. 1972. Elution of "blocking factors" from human tumors, capable of abrogating tumor-cell destruction by specifically immune lymphocytes. *Int J Cancer* 9:274-283.

38. Hellstrom, I., Hellstrom, K. E., and Sjogren, H. O. 1970. Serum mediated inhibition of cellular immunity to methylcholanthrene-induced murine sarcomas. *Cell Immunol* 1:18-30.

39. Sjogren, H. O., Hellstrom, I., Bansal, S. C., and Hellstrom, K. E. 1971. Suggestive evidence that the "blocking antibodies" of tumor-bearing individuals may be antigen-antibody complexes. *Proc Natl Acad Sci USA* 68:1372-1375.

40. Abusamra, A. J., Zhong, Z., Zheng, X., Li, M., Ichim, T. E., Chin, J. L., and Min, W. P. 2005. Tumor exosomes expressing Fas ligand mediate CD8+ T-cell apoptosis. *Blood Cells Mol Dis* 35:169-173.

41. Whiteside, T. L. 2005. Tumour-derived exosomes or microvesicles: another mechanism of tumour escape from the host immune system? *Br J Cancer* 92:209-211.

42. Kim, J. W., Wieckowski, E., Taylor, D. D., Reichert, T. E., Watkins, S., and Whiteside, T. L. 2005. Fas ligand-positive membranous vesicles isolated from sera of patients with oral cancer induce apoptosis of activated T lymphocytes. *Clin Cancer Res* 11:1010-1020.

43. Taylor, D. D., Gercel-Taylor, C., Lyons, K. S., Stanson, J., and Whiteside, T. L. 2003. T-cell apoptosis and suppression of T-cell receptor/CD3-zeta by Fas ligand-containing membrane vesicles shed from ovarian tumors. *Clin Cancer Res* 9:5113-5119.

44. Frangsmyr, L., Baranov, V., Nagaeva, O., Stendahl, U., Kjellberg, L., and Mincheva-Nilsson, L. 2005. Cytoplasmic microvesicular form of Fas ligand in human early placenta: switching the tissue immune privilege hypothesis from cellular to vesicular level. *Mol Hum Reprod* 11:35-41.

45. Taylor, D. D., Akyol, S., and Gercel-Taylor, C. 2006. Pregnancy-associated exosomes and their modulation of T cell signaling. *J Immunol* 176:1534-1542.

46. Mincheva-Nilsson, L., Nagaeva, O., Chen, T., Stendahl, U., Antsiferova, J., Mogren, I., Hernestal, J., and Baranov, V. 2006. Placenta-Derived Soluble MHC Class I Chain-Related Molecules Down-Regulate NKG2D Receptor on Peripheral Blood Mononuclear Cells during Human Pregnancy: A Possible Novel Immune Escape Mechanism for Fetal Survival. *J Immunol* 176:3585-3592.

47. Morelli, A. E. 2006. The immune regulatory effect of apoptotic cells and exosomes on dendritic cells: its impact on transplantation. *Am J Transplant* 6:254-261.

48. Peche, H., Heslan, M., Usal, C., Amigorena, S., and Cuturi, M. C. 2003. Presentation of donor major histocompatibility complex antigens by bone marrow dendritic cell-derived exosomes modulates allograft rejection. *Transplantation* 76:1503-1510.

49. Van Niel, G., Mallegol, J., Bevilacqua, C., Candalh, C., Brugiere, S., Tomaskovic-Crook, E., Heath, J. K., Cerf-Bensussan, N., and Heyman, M. 2003. Intestinal epithelial exosomes carry MHC class II/peptides able to inform the immune system in mice. *Gut* 52:1690-1697.

50. Ostman, S., Taube, M., and Telemo, E. 2005. Tolerosome-induced oral tolerance is MHC dependent. *Immunology* 116:464-476.

51. Erlanger, B. F. 1980. The preparation of antigenic hapten-carrier conjugates: a survey. *Methods Enzymol* 70:85-104.

52. Andreola, G., Rivoltini, L., Castelli, C., Huber, V., Perego, P., Deho, P., Squarcina, P., Accornero, P., Lozupone, F., Lugini, L., et al. 2002. Induction of lymphocyte apoptosis by tumor cell secretion of FasL-bearing microvesicles. *J Exp Med* 195:1303-1316.

53. Abrahams, V. M., Straszewski, S. L., Kamsteeg, M., Hanczaruk, B., Schwartz, P. E., Rutherford, T. J., and Mor, G. 2003. Epithelial ovarian cancer cells secrete functional Fas ligand. *Cancer Res* 63:5573-5581.

54. Valenti, R., Huber, V., Filipazzi, P., Pilla, L., Sovena, G., Villa, A., Corbelli, A., Fais, S., Parmiani, G., and Rivoltini, L. 2006. Human tumor-released microvesicles promote the differentiation of myeloid cells with transforming growth factor-beta-mediated suppressive activity on T lymphocytes. *Cancer Res* 66:9290-9298.

55. Janowska-Wieczorek, A., Marquez-Curtis, L. A., Wysoczynski, M., and Ratajczak, M. Z. 2006. Enhancing effect of platelet-derived microvesicles on the invasive potential of breast cancer cells. *Transfusion* 46:1199-1209.

56. Taylor, D. D., and Gercel-Taylor, C. 2005. Tumour-derived exosomes and their role in cancer-associated T-cell signalling defects. *Br J Cancer* 92:305-311.

57. Liu, C., Yu, S., Zinn, K., Wang, J., Zhang, L., Jia, Y., Kappes, J. C., Barnes, S., Kimberly, R. P., Grizzle, W. E., et al. 2006. Murine mammary carcinoma exosomes promote tumor growth by suppression of NK cell function. *J Immunol* 176:1375-1385.

58. Riteau, B., Faure, F., Menier, C., Viel, S., Carosella, E. D., Amigorena, S., and Rouas-Freiss, N. 2003. Exosomes bearing HLA-G are released by melanoma cells. *Hum Immunol* 64:1064-1072.

59. Clayton, A., and Tabi, Z. 2005. Exosomes and the MICA-NKG2D system in cancer. *Blood Cells Mol Dis* 34:206-213.

60. Parmiani, G., De Filippo, A., Novellino, L., and Castelli, C. 2007. Unique human tumor antigens: immunobiology and use in clinical trials. *J Immunol* 178:1975-1979.

61. Mocellin, S., Lise, M., and Nitti, D. 2007. Tumor immunology. *Adv Exp Med Biol* 593:147-156.

62. Hoos, A., Parmiani, G., Hege, K., Sznol, M., Loibner, H., Eggermont, A., Urba, W., Blumenstein, B., Sacks, N., Keilholz, U., et al. 2007. A clinical development paradigm for cancer vaccines and related biologics. *J Immunother* 30:1-15.

63. Dalgleish, A., and Pandha, H. 2007. Tumor antigens as surrogate markers and targets for therapy and vaccines. *Adv Cancer Res* 96:175-190.

64. Copier, J., and Dalgleish, A. 2006. Overview of tumor cell based vaccines. *Int Rev Immunol* 25:297-319.
65. Taylor, D. D., Gercel-Taylor, C., Lyons, K. S., Stanson, J., and Whiteside, T. L. 2003. T-cell apoptosis and suppression of T-cell receptor/CD3-zeta by Fas ligand-containing membrane vesicles shed from ovarian tumors. *Clin Cancer Res* 9:5113-5119.
66. Caby, M. P., Lankar, D., Vincendeau-Scherrer, C., Raposo, G., and Bonnerot, C. 2005. Exosomal-like vesicles are present in human blood plasma. *Int Immunol* 17:879-887.
67. Whiteside, T. L. 2004. Methods to monitor immune response and quality control. *Dev Biol (Basel)* 116:219-228; discussion 229-236.
68. Oldford, S. A., Robb, J. D., Codner, D., Gadag, V., Watson, P. H., and Drover, S. 2006. Tumor cell expression of HLA-DM associates with a Th1 profile and predicts improved survival in breast carcinoma patients. *Int Immunol* 18:1591-1602.
69. Marana, H. R., Silva, J. S., Andrade, J. M., and Bighetti, S. 2000. Reduced immunologic cell performance as a prognostic parameter for advanced cervical cancer. *Int J Gynecol Cancer* 10:67-73.
70. Kiaii, S., Choudhury, A., Mozaffari, F., Kimby, E., Osterborg, A., and Mellstedt, H. 2005. Signaling molecules and cytokine production in T cells of patients with B-cell chronic lymphocytic leukemia (B-CLL): comparison of indolent and progressive disease. *Med Oncol* 22:291-302.
71. Jones, F., H. Snyder and J. Balint (1998). Method for treatment of rheumatoid arthritis. USA, Cypress Bioscience, Inc., San Diego, Calif.
72. Snyder, H. W., Jr., J. P. Balint, Jr. and F. R. Jones (1989). "Modulation of immunity in patients with autoimmune disease and cancer treated by extracorporeal immunoadsorption with PROSORBA columns." *Semin Hematol* 26(2 Suppl 1): 31-41.
73. Cuatrecasas, P., M. Wilchek and C. B. Anfinsen (1968). "Selective enzyme purification by affinity chromatography." *Proc Natl Acad Sci USA* 61(2): 636-43.
74. Gold, L. (1995). "The SELEX process: a surprising source of therapeutic and diagnostic compounds." *Harvey Lect* 91: 47-57.
75. Gold, L. and S. Ringquist (1996). Systematic evolution of ligands by exponential enrichment: Solution SELEX. USA, University Research Corporation (Boulder, Co.).
76. Hermanson, G. T. (1996). Bioconjugate *Techniques:* 785.

The embodiments of the invention in which an exclusive property or privilege is claimed are defined as follows:

1. A method of capturing an exosome from a patient on a surface that comprises a lectin, said method comprising:
   identifying a patient for exosome capture and contacting an exosome from said patient with a surface that comprises a lectin thereby capturing said exosome.
2. The method of claim 1, wherein the surface is selected from the group consisting of: silica gel, dextran, agarose, nylon polymers, polymers of acrylic acid, silica gel, dextran, agarose, nylon polymers, polymers of acrylic acid, co-polymers of ethylene and maleic acid anhydride, aminopropylsilica, aminocelite, glass beads, and silicate containing diatomaceous earth.
3. The method of claim 1, wherein the surface is a bead.
4. The method of claim 1, wherein the surface is a filter.
5. The method of claim 1, wherein the lectin is selected from the group consisting of GNA, NPA, Conconavalin A, phytohemagluttanin, and cyanovirin.
6. The method of claim 1, wherein the patient has cancer.
7. The method of claim 1, wherein the patient has spontaneous T cell apoptosis.
8. The method of claim 1, wherein the exosome is from whole blood or components thereof.
9. A method of capturing an exosome from a patient comprising:
   contacting an exosome from said patient with an affinity device that comprises an affinity absorbent comprising a lectin thereby capturing said exosome on the affinity absorbent.
10. The method of claim 9, wherein the affinity absorbent comprises silica gel, dextran, agarose, nylon polymers, polymers of acrylic acid, silica gel, dextran, agarose, nylon polymers, polymers of acrylic acid, co-polymers of ethylene and maleic acid anhydride, aminopropylsilica, aminocelite, glass beads, or silicate containing diatomaceous earth.
11. The method of claim 9, wherein the affinity absorbent is a bead.
12. The method of claim 9, wherein the affinity absorbent is a filter.
13. The method of claim 9, wherein the lectin is selected from the group consisting of GNA, NPA, Conconavalin A, phytohemagluttanin, and cyanovirin.
14. The method of claim 9, wherein the patient has cancer.
15. The method of claim 9, wherein the patient has spontaneous T cell apoptosis.
16. The method of claim 9, wherein the exosome is from whole blood or components thereof.
17. The method of claim 9, further comprising selecting a patient to have an exosome captured by said affinity device.

* * * * *